United States Patent [19]

Ishikawa et al.

[11] Patent Number: 5,202,329

[45] Date of Patent: Apr. 13, 1993

[54] PYRIMIDINYLOXY(THIO)QUINOLINE DERIVATIVE, AND AGRI-HORTICULTURAL FUNGICIDE COMPRISING THE DERIVATIVE AS ACTIVE INGREDIENT

[75] Inventors: Katsutoshi Ishikawa; Yukihiro Yoshikawa; Tsutomu Ishii; Hiroharu Tanikawa; Sunao Maeda; Hideo Kawashima; Yuji Yanese, all of Mobara; Hitoshi Shimotori, Chiba; Ryuichi Mita, Ohmuta, all of Japan

[73] Assignee: Mitsui Toatsu Chemicals Inc., Tokyo, Japan

[21] Appl. No.: 849,714

[22] Filed: Mar. 11, 1992

Related U.S. Application Data

[63] Continuation-in-part of Ser. No. 828,311, Jan. 30, 1992.

[30] Foreign Application Priority Data

Jan. 31, 1991 [JP] Japan .................... 3-10648
Apr. 25, 1991 [JP] Japan .................... 3-95122

[51] Int. Cl.[5] ............... C07D 239/24; C07D 239/38; A01N 43/54
[52] U.S. Cl. ......................... 514/274; 514/270; 544/300; 544/310; 544/316
[58] Field of Search ............... 514/270, 274; 544/300, 544/310, 316

[56] References Cited

U.S. PATENT DOCUMENTS 4,808,591 2/1989 Santini .................... 514/274

FOREIGN PATENT DOCUMENTS 0326330 8/1989 European Pat. Off. .
2205101 11/1988 United Kingdom .

OTHER PUBLICATIONS

Chemical Abstracts, vol. 93, 1980, Abstract No. 239180r.

Primary Examiner—John M. Ford
Attorney, Agent, or Firm—Millen, White, Zelano and Branigan

[57] ABSTRACT

Pyrimidinyloxy(thio)quinoline derivatives represented by the formula (I) which exhibit an excellent controlling effect for plant diseases and are also safe for crop plants, preparation processes of the derivatives, and agri-horticultural fungicides comprising the derivatives as an active ingredient, are disclosed.

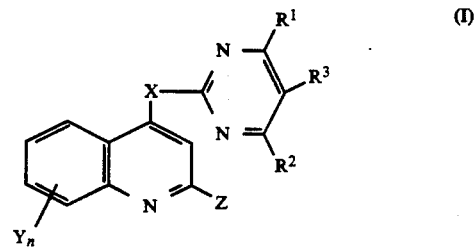

In the formula (I), X is an oxygen atom or sulfur atom, Y is a hydrogen atom or halogen atom, Z is a hydrogen atom or methyl, $R^1$ and $R^2$ are methoxy or methyl, and n is an integer of 1 or 2.

20 Claims, No Drawings

PYRIMIDINYLOXY(THIO)QUINOLINE DERIVATIVE, AND AGRI-HORTICULTURAL FUNGICIDE COMPRISING THE DERIVATIVE AS ACTIVE INGREDIENT

CROSS-REFERENCE TO RELATED APPLICATION

This application is a continuation-in-part of Ser. No. 07/828,311, pending filed Jan. 30, 1992.

BACKGROUND OF THE INVENTION

1. Field of the Invention

The present invention relates to a novel pyrimidinyloxy(thio) quinoline derivative, preparation process of the derivative, and an agri-horticultural fungicide comprising the derivative as an active ingredient.

2. Related Art of the Invention

European Patent 326330 has disclosed that quinolines having aryloxy or arylthio at the position-4 have fungicidal activity.

However, the compounds described in the patent have primarily substituted phenyl as aryl groups. Heterocyclic groups disclosed are merely each one or two examples of pridyl, pyridazinyl, pyrazolyl and tetrazolyl, respectively. It is described that these heterocyclic groups exhibit very low or no controlling effect for diseases. Consequently, the subject matter of the above patent is that quinolines having substituted phenoxy at the position-4 of quinoline ring have an excellent controlling effect for diseases. The present inventors have conventionally paid attention to the good affinity of pyrimidines for organism and have investigated development of physiologically active substances. Accordingly, they have focused attention to the fact that quinolines having pyrimidinyloxy or pyrimidinylthio at the position-4 are novel compounds and have not yet been investigated at all, and have started investigation. For the purpose of comparison, compounds which are described to be excellent in the above patent have been tested. As a result, compounds having high controlling effect have caused chemical injury for crop plants, and those having low chemical injury have led to low controlling effect and been unsuitable for practical use.

SUMMARY OF THE INVENTION

An object of the present invention is to provide a novel pyrimidinyloxy(thio)quinoline derivative which is a compound exhibiting an excellent fungicidal effect and at the same time being safe for crop plants.

Another object of the present invention is to provide a process for preparing the novel compound.

A further object of the present invention is to provide an agri-horticultural fungicide comprising the compound and a method for applying the fungicide.

As a result of an intensive investigation in order to achieve the above objects, the present inventors have found that the compound of the present invention has superior fungicidal effect to the conventional compounds and simultaneously exhibits excellent safety for crop plants such as cucumbers, tomatoes, grapes and wheat. Thus the present invention has been completed.

One aspect of the present invention is a pyrimidinyloxy(thio) quinoline derivative represented by the formula(I):

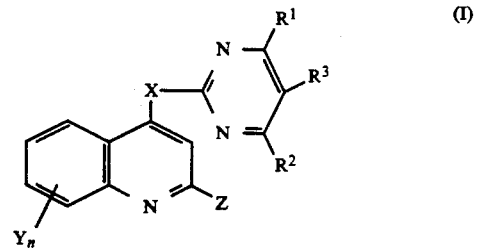

wherein X is an oxygen atom or sulfur atom, Y is a hydrogen atom, halogen atom, alkyl having from 1 to 3 carbon atoms, alkoxy having from 1 to 3 carbon atoms, or trifluoromethyl, Z is a hydrogen atom or methyl, each of $R^1$ and $R^2$ is individually in alkyl having from 1 to 4 carbon atoms, alkoxy having from 1 to 3 carbon atoms, trifuluromethyl or hydrogen atom, $R^3$ is a hydrogen atom or alkyl having from 1 to 2 carbon atoms, and n is an integer of 1 or 2.

Another aspect of the present invention is a process for preparing a pyrimidinyloxy(thio)quinoline derivative of the formula (I) by mixing and reacting a 4-chloroquinoline derivative represented by the formula (II):

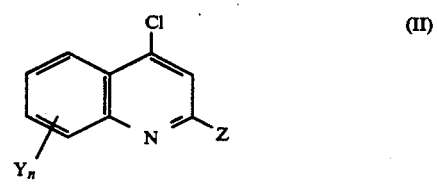

wherein Y is a hydrogen atom, halogen atom, alkyl having from 1 to 3 carbon atoms, alkoxy having from 1 to 3 carbon atoms, or trifluoromethyl, Z is a hydrogen atom or methyl, and n is an integer of 1 or 2, with a pyrimidine derivative represented by the formula (III):

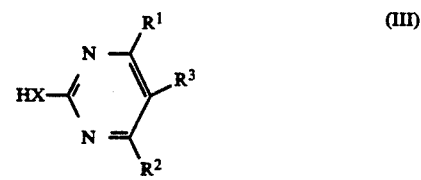

wherein X is an oxygen atom or sulfur atom, each of $R^1$ and $R^2$ is individually an alkyl having from 1 to 4 carbon atoms, alkoxy having from 1 to 3 carbon atoms, trifluoromethyl or hydrogen atom, and $R^3$ is a hydrogen atom or alkyl having from 1 to 2 carbon atoms in a molten state or in the presence of an inert solvent.

A further aspect of the present invention is a preparation process of a pyrimidinyloxy(thio)quinoline derivative of the formula (I) by reacting a 4-hydroxy(or mercapto)quinoline derivative represented by the formula (IV):

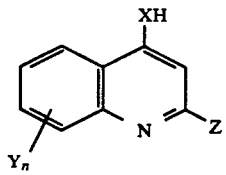

wherein X is an oxygen atom or sulfur atom, Y is a hydrogen atom, halogen atom, alkyl having from 1 to 3 carbon atoms, alkoxy having from 1 to 3 carbon atoms or trifluoromethyl, Z is a hydrogen atom or methyl, and n is an integer of 1 or 2, with a 2-chloropyrimidine derivative represented by the formula (V):

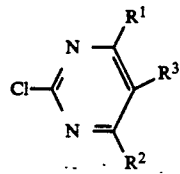

wherein each of $R^1$ and $R^2$ are individually an alkyl having from 1 to 4 carbon atoms, alkoxy having from 1 to 3 carbon atoms, trifluoromehtyl or hydrogen atom, and $R^3$ is a hydrogen atom or alkyl having from 1 to 2 carbon atoms, after converting the 4-hydroxy(or mercapto)quinoline derivative to a metal salt or in the presence of a base.

Still another aspect of the present invention is a preparation process of a pyrimidinyloxy(thio) quinoline derivative of the formula (I) by reacting a 4-chloroquinoline derivative of the formula (II):

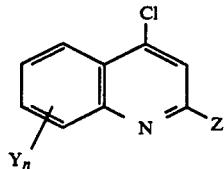

wherein Y, Z and n are the same as above, with a pyrimidine derivative represented by the formula (III):

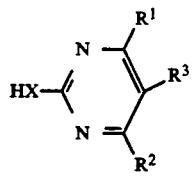

wherein X is a sulfur atom and $R^1$, $R^2$ and $R^3$ are the same as above, in the presence of a base.

A still further aspect of the present invention is an agrihorticultural fungicide comprising a pyrimidinyloxy(thio)quinoline derivative as an active ingredient.

Another aspect of the present invention is a controlling method of plant disease comprising applying a pyrimidinyloxy(thio)quinoline derivative to plant pathogenic fungi or their habitat.

The agri-horticultural fungicide comprising the compound represented by the formula (I) of the invention exhibits a remarkable controlling effect with a low dose for disease damage which causes problems in agriculture and horticulture. The fungicide exerts a dominant effect particularly for powdery mildew. On the other hand, the fungicide is extremely safe for crop plants such as cucumbers and wheat. In view of recent development of a resistant strain for azolbase fungicides, the present invention provides an excellent agrihorticultural fungicide which can replace the azol-base fungicides.

DETAILED DESCRIPTION OF THE INVENTION

The novel pyrimidinyloxy(thio)quinoline derivative of the present invention is a compound represented by the formula (I):

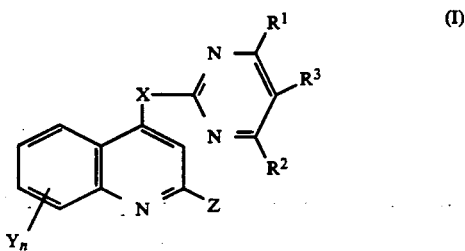

In the formula (I), the substituent represented by Y is an alkyl having from 1 to 3 carbon atoms, i.e., methyl, ethyl, n-propyl or isopropyl; or alkoxy having from 1 to 3 carbon atoms, i.e., methoxy, ethoxy, n-propoxy or isopropoxy. $Y_n$ is halogen substituents and preferably 7-chloro, 7-bromo, 7-iodo, 5,7-dichloro, 5,7-dibromo or 5,7-diiodo. Z is preferably a hydrogen atom. The substituents represented by $R^1$ and $R^2$ are individually an alkyl having from 1 to 4 carbon atoms, i.e., methyl, ethyl, n-propyl, isopropyl, n-butyl, isobutyl, sec-butyl or tert-butyl; or an alkoxy having from 1 to 3 carbon atoms, i.e., methoxy, ethoxy, n-propoxy or isopropoxy. The substituent represented by $R^3$ is a hydrogen atom or an alkyl having 1 or 2 carbon atoms, i.e., methyl or ethyl and preferably a hydrogen atom.

The compound of the invention can be prepared by below described processes (A), (B) and (C).

Process A:

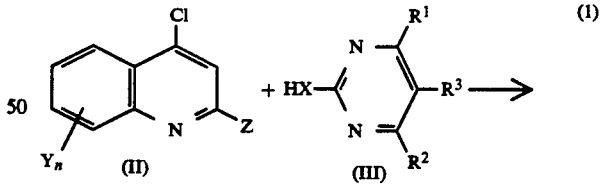

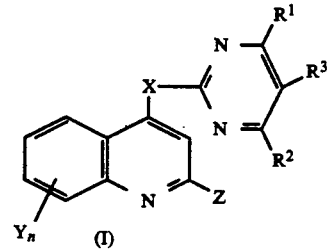

Syntheses of an ether bond and a sulfide bond are usually carried out by reacting a halogen compound with hydroxide or mercaptan in the presence of a base. However, as a result of an extensive investigation, the inventors have found that the compound of the invention can be obtained by mixing and heating the starting materials, that is, the compounds of the formula (II) and the formula (III), or, in some cases, by merely adding an inert solvent to provide flowability for the starting materials and successively heating the mixture.

The reaction conditions will hereinafter be illustrated in detail.

The compound of the formula (III) wherein X is sulfur has better reactivity. The reaction temperature is usually from room temperature to 200° C. preferably from 70° to 90° C. The compound of the formula (III) wherein X is oxygen has somewhat inferior reactivity and requires higher reaction temperature as compared with the compound wherein X is a sulfur atom. The reaction temperature is usually from 100° to 200° C., preferably from 110° to 150° C. The reaction time depends upon the reaction temperature and is usually from 1 to 10 hours to complete the reaction.

Any solvent can be used so long as the solvent is inert in the reaction of the invention and has a boiling point higher than the reaction temperature. Exemplary solvents which can be used include aromatic hydrocarbons such as benzene, toluene, and xylene; ethers such as dioxane and diglyme; aprotic polar solvents such as dimethylformamide, dimethylimidazolidinone and dimethyl sulfoxide; and acetonitrile.

The intermediate 4-chloroquinoline derivative represented by the formula (II) can be obtained from the market or prepared by one of the processes described below.

(1) Z is a hydrogen atom (case 1)

The compound can be prepared in accordance with the following reaction path which is described in Organic Syntheses, Col. Vol. 3, 272(1955).

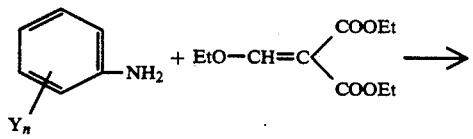

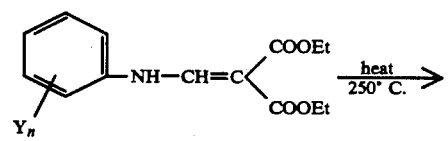

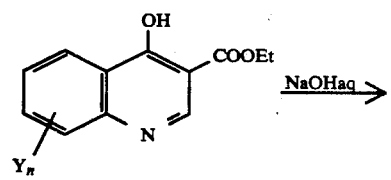

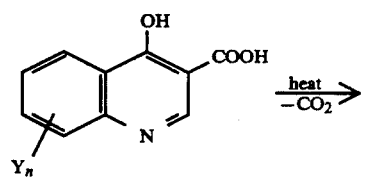

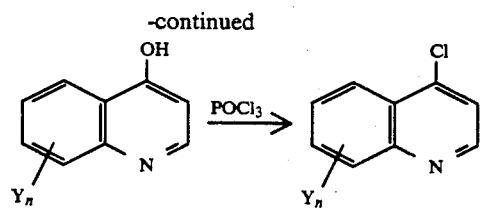

(2) Z is a hydrogen atom (case 2)

The compound can also be prepared in accordance with the following reaction path by using methoxymethylene Meldrum's acid in place of diethyl ethoxymethylenemalonate in the above process (1).

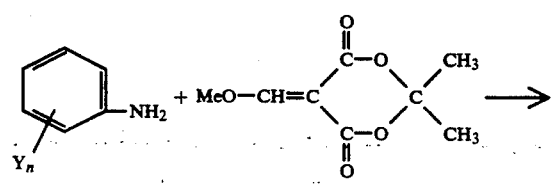

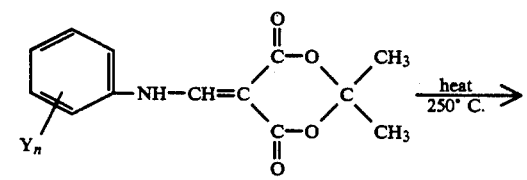

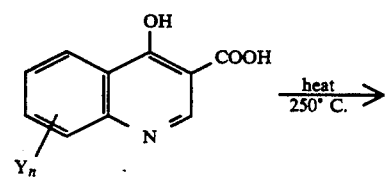

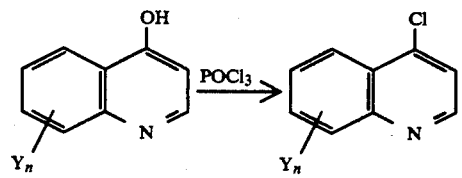

(3) Z is an atom other than hydrogen

The compound can be prepared in accordance with the following reaction path which is described in J. Am. Chem. Soc. 66, 621(1944).

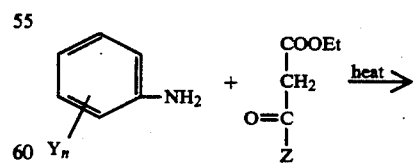

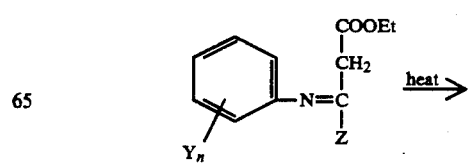

-continued

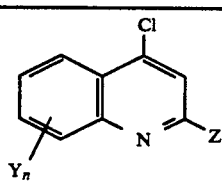

Both known and novel 4-chloroquinoline derivatives have been prepared in accordance with the above paths (1), (2) and (3). Known 4-chloroquinoline derivatives are exemplified in Table 1. Table 2 illustrates examples of novel 4-chloroquinoline derivatives.

TABLE 1

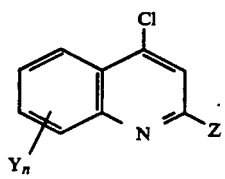

| $Y_n$ | Z | mp (°C.) | Literature |
|---|---|---|---|
| H | H | oil | Ber., 59, 1848 (1926) |
| 7-Cl | H | 83.5~84.5 | J. Amer. Chem. Soc., 68, 1299 (1946) |
| 6-Cl | H | 105.1~106.6 | J. Chem. Soc., 1950, 384 |
| 8-Cl | H | 156.3~157.8 | J. Med. Chem., 12, 797 (1969) |
| 7-Cl | Me | 103 | J. Amer. Chem. Soc., 66, 621 (1944) |
| 5-Cl | Me | 89 | J. Amer. Chem. Soc., 66, 621 (1944) |
| 6-F | H | 77 | J. Amer. Chem. Soc., 69, 371 (1947) |
| 7-F | H | 74 | J. Amer. Chem. Soc., 69, 371 (1947) |
| 8-F | H | 91~94 | C.A., 112 (7), 55630s |
| 7-Br | H | 99.3~100.2 | J. Amer. Chem. Soc., 68, 1299 (1946) |
| 5-Cl | H | 115.5~116.5 | J. Amer. Chem. Soc., 68, 1299 (1946) |
| 7-I | H | 100.6~101.8 | J. Amer. Chem. Soc., 68, 1299 (1946) |
| 5,7-Cl$_2$ | H | 105.8~107.3 | J. Med. Chem., 12, 797 (1969) |
| 6,7-Cl$_2$ | H | 121.3~122.2 | J. Amer. Chem. Soc., 68, 1244 (1946) |
| 7,8-Cl$_2$ | H | 126 | J. Amer. Chem. Soc., 68, 1244 (1946) |
| 7-CF$_3$ | H | 63.0~64.5 | J. Amer. Chem. Soc., 69, 371 (1947) |
| 7-OMe | H | 84.6~85.4 | J. Amer. Chem. Soc., 68, 1268 (1946) |
| 7-Me | H | oil | J. Amer. Chem. Soc., 68, 1232 (1946) |
| 6-Me | H | 55 | J. Amer. Chem. Soc., 70, 1363 (1948) |
| 5,7-Me$_2$ | H | 59 | J. Amer. Chem. Soc., 70, 1363 (1948) |

TABLE 2
(Novel 4-chloroquinoline derivative)

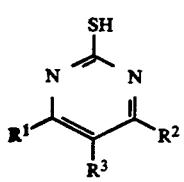

| Yn | Z | mp (°C.) | perparation path |
|---|---|---|---|
| 7-Br | Me | 102~103 | (3) |

TABLE 2-continued
(Novel 4-chloroquinoline derivative)

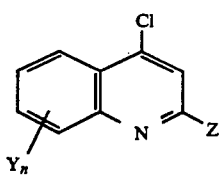

| Yn | Z | mp (°C.) | perparation path |
|---|---|---|---|
| 7-Br | Me | 95~96.5 | (3) |
| 5-I | H | 88.8~90.0 | (3) |
| 7-I | Me | 79~81 | (3) |
| 5,7-I$_2$ | H | 168~170 | (3) |
| 5-Me | H | oil | (3) |
| 5,7-(OMe)$_2$ | H | 77 | (3) |

Another intermediate pyrimidine derivative can be obtained in the market or prepared by the processes described below.

(1) X is an oxygen atom

The pyrimidine derivative can be obtained by diazotizing the corresponding amino compound and successively hydrolyzing the resulting intermediate according to the following reaction formula. A chloro derivative can also be formed by using HCl.

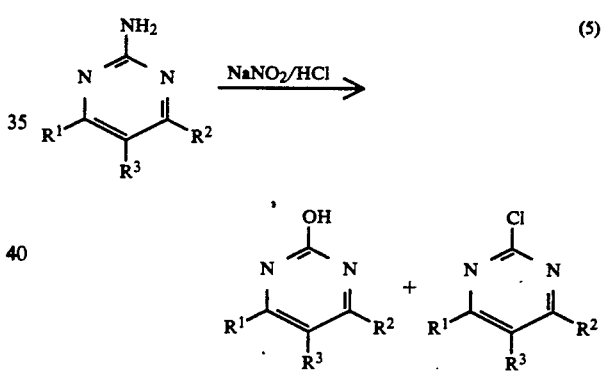

(5)

(2) X is a sulfur atom

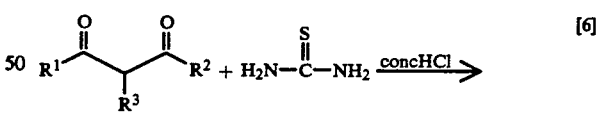

[6]

Many of these pyrimidine derivatives are conventionally known compounds. However, 4,6-diethyl-2-mercaptopyrimidine and 2-mercapto-4-methyl-6-trifluoromethylpyrimidine have not yet been described in the literature.

Next, another preparation process of the quinoline compound represented by the formula (I) will be described.

The compound represented by the formula (I) can also be prepared through a combined process described below.

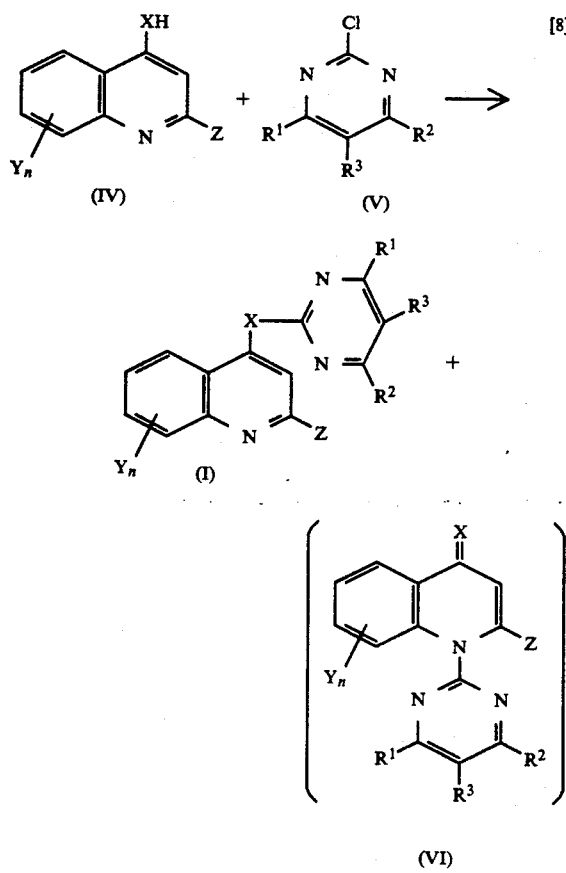

[8]

In the case of the combined process, the compound of the formula (IV) wherein X is an oxygen atom can give very low yield or no yield of the desired compound of the formula (I) and provides the compound of the formula (VI) as a main product. On the other hand, the compound wherein X is sulfur can smoothly progress the reaction and affords the desired product of the formula (I) in a high yield. The process will be illustrated below further in detail. Process B: X is an oxygen atom The compound of the formula (VI) is usually obtained by using common bases such as alkali hydroxide, alkali carbonate, sodium hydride or metallic sodium. The present inventors have found that the compound of the formula (I) can be obtained by converting the compound of the formula (VI) to a Ag salt. The Ag salt of the compound of the formula (IV) can be readily obtained in the form of precipitate by adding AgNO₃ to an aqueous sodium hydroxide solution of the compound of the formula (IV). After azeotropically dehydrated by benzene or toluene, the Ag salt is reacted with a 2-chlorpyrimidine derivative in an inert solvent such as dimethylimidazolidinone to obtain the compound of the formula (I).

Process C: X is an sulfur atom

The desired reaction can progress in the presence of a base and N-substituted compound such as the compound of the formula (I) is not formed. The bases which can be used include, for example, metallic sodium, sodium hydride, alkali hydroxide, alkali carbonate and organic bases such as triethylamine. Any solvents can be used so long as the solvents are inert in the reaction.

The reaction temperature is generally in the range of from 0° C. to the boiling point of the solvent, preferably from 20° to 80° C.

The intermediate 4-mercaptoquinoline derivative can be prepared by reacting the 4-chloroquinoline derivative with thiourea in accordance with the process described in J. Am. Chem. Soc., 70, 2190(1948). Another intermediate 2-chloropyrimidine derivative is formed together with the 2-hydroxypyrimidine derivatives as mentioned in the reaction [5].

The present invention is an agri-horticultural fungicide comprising the compound represented by the formula (I) as an active ingredient.

The agri-horticultural fungicide of the invention exhibits an excellent controlling effect on plant diseases such as cucumber powdery mildew, barley powdery mildew, wheat powdery mildew, strawberry powdery mildew, tomato powdery mildew, grape powdery mildew, cucumber anthracnose, wheat brown rust, apple scab, apple leaf spot, apple powdery mildew, pear scab, and pear black spot.

On using the compound of the formula (I) in the present invention for the agri-horticultural fungicide, the intact technical product can be applied to the plant to be treated. The technical product, however, is generally mixed with an inert liquid or solid carrier, and used in the form of dust formulation, wettable powder, floable formulation, emulsifiable concentrate, granule and other commonly used formulations. Further, adjuvants can be added if required for formulating the compound of the invention.

The term carrier refers to a synthetic or natural, inorganic or organic substance which is formulated in order to assist deposit of the active ingredient to the site to be treated and to make storage, transport and handling of the active ingredient easy. No particular restriction is imposed upon the carrier. Both solid and liquid carriers can be used so long as they are commonly employed for agri-horticultural chemicals.

Solid carriers include, for example, clays such as montmorillonite and kaolinite; inorganic materials such as diatomaceous earth, acid clay, talc, vermiculite, gypsum, calcium carbonate, silica gel and ammonium sulfate; and organic materials such as soybean flour, sawdust, wheat flour and urea.

Exemplary liquid carriers include aromatic hydrocarbons such as toluene, xylene and cumene; paraffin hydrocarbons such as kerosene and mineral oil; halogenated hydrocarbons such as carbon tetrachloride, chloroform, and dichloroethane; ketones such as acetone and methyl ethyl ketone; ethers such as dioxane and diethylene glycol dimethyl ether; alcohols such as methanol, ethanol, propanol and ethylene glycol; and dimethylformamide, dimethyl sulfoxide and water.

Adjuvants can also be added singly or in combination in order to enhance activity of the compound of the invention depending upon the object in view of formulation and application site.

Adjuvants which can be used include, for example, surface active agents which are commonly used for agri-horticultural chemicals; binders such as ligninsulfonic acid, alginic acid, polyvinyl alcohol, gum arabic, and sodium carboxymethyl cellulose; antioxidants such as phenol-base compound, thiol-base compound and higher fatty acid ester; pH regulators such as phosphoric acid salt; and UV-absorbers. These adjuvants are used singly or in combination depending upon requirement. Further, industrial bactericide or antimold can also be added in order to control fungi and bacteria.

Other adjuvants which can be used for the purpose of emulsification, dispersion, spreading, moistening, combination and stabilization include, for example, anionic surface active agents such as ligninsulfonate, alkylbenzenesulfonate, alkylestersulfate, polyoxyalkylene alkylsulfate and polyoxyalkylene alkylphosphate; nonionic surface active agents such as polyoxyalkylene alkyl ether, polyoxyalkylene alkylaryl ether, polyoxyalkylenealkylamine, polyoxyalkylenealkylamide, polyoxyalkylene alkyl thioether, polyoxyalkylene fatty acid ester, glycerol fatty acid ester, sorbitan fatty acid ester, polyoxyalkylenesorbitan fatty acid ester and polyoxypropylene polyoxyethylene block copolymer; lubricants such as calcium stearate and waxes; stabilizers such as isopropyl hydrogen phosphate; and methyl cellulose, carboxymethyl cellulose, casein and gum arabic. However, no particular restriction is imposed upon the above adjuvants.

The content of the compound represented by the formula (I) in the agri-horticultural fungicide of the invention differs depending upon the morphology of formulation and generally from 0.05 to 20% by weight in dust formulation, from 0.1 to 80% by weight in water dispersible powder, from 1 to 50% by weight in emulsifiable concentrate, from 1 to 50% by weight in floable formulation, and from 1 to 80% by weight in dryfloable formulation; preferably from 0.5 to 5% by weight in dust formulation, from 5 to 80% by weight in water dispersible powder, from 0.5 to 8% by weight in granule, from 5 to 20% by weight in emulsifiable concentrate, from 5 to 30% by weight in floable formulation and from 5 to 50% by weight in dryfloable formulation.

The content of the adjuvant is from 0 to 80% by weight and the content of the carrier is an amount obtained by subtracting the total content of the active compound and adjuvant from 100% by weight.

Representative application method of the formulation of the invention includes seed disinfection and foliage application. However, any application method commonly utilized by those who are skilled in the art can exhibit satisfactory effect. The amount and concentration in the application variate depending upon the target crop, target disease developed degree of disease damage, formulation of the active compound, application method and various environmental conditions. In the case of spraying, the amount of the active ingredient is suitably from 2 to 200 g/ha, preferably from 5 to 100 g/ha. When a wettable powder, a suspended concentration or an emulsifiable concentrate is sprayed after diluting with water, the dilution is generally from 500 to 20,000 times, preferably from 1,000 to 10,000 times.

The present invention will hereinafter be illustrated further in detail.

EXAMPLE 1

Synthesis (Process A) of
7-chloro-4-(4,6-dimethoxy-2-pyrimidinyloxy)quinoline

Compound No. 1

To 3.65 g of 4,7-dichloroquinoline, 1.56 g of 4,6-dimethoxy-2-hydroxypyrimidine and 5 ml of N,N-dimethylimidazolidinone were added and heated at 120° C. for 5 hours.

The reaction mixture was cooled and separated by silica gel column chromatography(n-hexane/ethyl acetate=7/3) to obtain 7-chloro-4-(4,6-dimethoxy-2-pyrimidinyloxy)quinoline. Yield was 1.53 g. Melting point was 119°-120° C.

NMR(CDCl$_3$)δ: 3.81(6H,s), 5.87(1H,s), 7.30(1H,d,J=5.1 Hz), 7.50(1H,dd,J=2.20 Hz,8.80 Hz), 8.06(1H,d,J=8.80 Hz), 8.14(1H,d,J=2.20 Hz), 8.91(1H,d,J=5.1 Hz)

EXAMPLE 2

Synthesis (process A) of
8-chloro-(4,6-dimethoxy-2-pyrimidinyloxy)quinoline

Compound No. 2

To 2.0 g of 4,8-dichloroquinoline, 3.0 g of 4,6-dimethoxy-2-hydroxypyrimidine and 5 ml of N-dimethylimidazolidinone were added and heated at 120°-130° C. for 10 hours.

The reaction mixture was cooled and separated by silica gel columnchromatography(n-hexane/ethyl acetate=7/3) to obtain 8-chloro-4-(4,6-dimethoxy-2-pyrimidinyloxy)quinoline. Yield was 1.25 g. Melting point was 115°-118° C.

NMR(CDCl$_3$)δ: 3.81(6H,s), 5.87(1H,s), 7.38(1H,d,J=4.8 Hz), 7.46(1H,t,J=8.0 Hz), 8.06(1H,d,J=8.0 Hz), 9.05(1H,d,J=4.8 Hz)

EXAMPLE 3

Synthesis (process A) of
7-chloro-4-(4,6-dimethyl-2-pyrimidinylthio)-quinoline

Compound No. 3

A mixture of 1.17 g of 4,7-dichloroquinoline, 1.0 g of 4,6-dimethyl-2-mercaptopyrimidine and 3 ml of N,N-dime thylimidazolidinone was heated at 80° C. for 1 hour. The reaction mixture was cooled and separated by column chromatography(n-hexane/ethyl acetate=1/1) to obtain . 7-chloro-4-(4,6-dimethyl-2-pyrimidinylthio)-quinoline. Yield was 0.83 g. Melting point was 127.4°-129.5° C.

NMR(CDCl$_3$)δ: 2.30(6H,s), 6.75(1H,s), 7.47(1H,m), 7.84(1N,d, J=4,4 Hz), 8.12(1H,S), 8.14(1H,m), 8.90(1H,d, J=4,4 Hz)

EXAMPLE 4

Synthesis (Process A) of
5,7-dichloro-4-(4,6-dimethyl-2-pyrimidinylthio)quinoline Compound No. 19

A solution was prepared by dissolving 15.7 g of 4,5,7-trichloroquinoline in 60 ml of dry dimethylimidazolidinone. To the solution, 10.4 g of 4,6-dimethyl-2-mercaptopyrimidine was added with stirring at the room temperature. The reaction was progressed with heat evolution and the temperature of the reaction mixture was increased to 50° C. Crystals were precipitated in the course of the reaction. After finishing the addition, stirring was continued for about 2 hours to complete the reaction. The reaction mixture was mixed with 300 ml of water. Precipitated crystals were filtered and recrystallized from acetone to obtain 20.8 g (91.9% yield) of 5,7-dichloro-4-(4,6-dimethyl-2-pyrimidinylthio)quinoline. Melting point was 182.0°-183.2° C.

NMR(CDCl$_3$)δ: 2.31(6H,s), 6.77(1H,s), 7.58(1H,d,J=2,2 Hz), 7.76(1H,d,J=5.1 Hz), 8.09(1H,d,J=2.2 Hz), 8.83(1H,d,J=5.1 Hz)

EXAMPLE 5

Synthesis (Process B) of 7-chloro-4-(4,6-dimethyl-2-pyrimidinyloxy)quinoline Compound No. 262

To an aqueous solution containing 0.28 g of sodium hydroxide in 8.5 ml of water, 0.90 g of 7-chloro-4-hydroxyquinoline was added and dissolved by warming to 60°-70° C. After cooling the resulting solution, an aqueous solution containing 0.85 g of silver nitrate in 2 ml of water was added. Light gray precipitate was formed. After 10 minutes, 20 ml of dimethylimidazolidinone and 20 ml of benzene were added and azeotropic dehydration was carried out from 75° to 140° C. to obtain dehydrated silver salt. Successively, 0.86 g of 2-chloro-4,6-dimethylpyrimidine was added at 90°-110° C. and heated at 100°-150° C. for 9 hours. The reaction mixture was cooled and insoluble matter was filtered. Solvent was distilled off from the filtrate and the residue was separated by silica gel column chromatography(eluate; ethyl acetate) to obtain 0.29 g (20% yield) of desired product 7-chloro-4-(4,6-dimethyl-2-pyrimidinyloxy)quinoline. Melting point was 104°-105° C.

NMR(CDCl$_3$)$\delta$: 2.46(6H,s), 6.91(1H,s), 7.27(1H,d,J=4.4 Hz), 7.50(1H,dd,J=2.2, 8.8 Hz), 8.13(1H,d,J=8.8 Hz), 8.14(1H,d,J=2.2 Hz), 8.89(1H,d,J=4,4 Hz)

EXAMPLE 6

Synthesis (Process C) of 7-chloro-4-(4,6-dimethoxy-2-pyrimidinylthio)quinoline Compound No. 263

(1) 7-Chloro-4-mercaptopyrimidine (intermediate)

To 250 ml of ethanol, 25 g of 4,7-dichloroquinoline was added and warmed to 50° C. Successively, 9.7 g of thiourea was added. After about 5 minutes, large amount of crystals was precipitated. The crystals were filtered and added to an aqueous sodium carbonate solution and stirred. Separated orange crystals were filtered and poured into 250 ml of a 5% aqueous sodium hydroxide solution and stirred for some time. Insoluble matter was filtered off. The filtrate was neutralized with acetic acid. The precipitated crystals were filtered and dried to obtain 19.6 g (80% yield) of the desired intermediate 7-chloro-4-mercaptopyrimidine as yellow crystals. Melting point was 199.8°-200.5° C.

NMR(DMSO-d$_6$)$\delta$: 7.29(1H,d,J=6.6 Hz), 7.46-7.49(1H,m), 7.71(1H,d, J=2.2 Hz), 7.88(1H,d,J=6.6 Hz), 8.66(1H,d,J=8.8 Hz)

(2) 7-Chloro-4-(4,6-dimethoxy-2-pyrimidinylthio)quinoline

To 15 ml of dimethylimidazolidinone, 0.13 g of 60% sodium hydride and 0.5 g of 7-chloro-4-mercaptoquinoline were added and stirred at 60° C. for 1 hour. Successively, 0.45 g of 2-chloro-4,6-dimethoxypyrimidine was added and stirred at 50°-60° C. for 2.5 hours. After finishing the reaction, the reaction mixture was poured into water and extracted 3 times with 100 ml of ethyl acetate. Ethyl acetate layer was washed with water, dried over anhydrous sodium sulfate and distilled off the solvent. The residue was separated by silica gel column chromatography (eluate; n-hexane/ethyl acetate= 1/1) to obtain 0.25 g (30% yield) of the desired product 7-chloro-4-(4,6-dimethoxy-2-pyrimidinylthio)-quinoline. Melting point was 93.0°-94.5° C.

NMR(CDCl$_3$)$\delta$: 3.55(6H,s), 5.72(1H,s), 7.51(1H,dd,J=9.5 & 2.2 Hz), 7.80(1H,d,J=4.4 Hz), 8.14(1H,d,J=2.2 Hz), 8.24(1H,d,J=9.5 Hz), 8.92(1H,d,J=4.4 Hz)

EXAMPLE 7

Synthesis (Process A) of 7-chloro-4-(4,6-diethyl-2-pyrimidinylthio)quinoline Compound No. 78

(1) 4,6-Diethyl-2-mercaptopyrimidine (intermediate)

After dissolving 8.1 g of thiourea and 15.0 g of heptane-3,5-dione in 290 ml of ethanol, 29 ml of concentrated hydrochloric acid was added dropwise with stirring at the room temperature. Successively, the mixture was stirred for 3 hours under reflux. The reaction mixture was allowed to cool and poured into 300 ml of water and extracted 3 times with 150 ml of diethyl ether. Water layer was adjusted to pH12 with a 50% aqueous sodium hydroxide solution, further extracted 3 times with 150 ml of diethyl ether. Aqueous layer was neutralized to pH 4 with acetic acid and extracted 3 times with 200 ml of dichloromethane. The organic solvent layer was washed with an aqueous sodium hydrogen carbonate solution and dried over anhydrous sodium sulfate. The solvent was distilled off under reduced pressure to obtain 9.45 g (53% yield) of desired intermediate 4,6-diethyl-2-mercaptopyrimidine. Melting point was 82.0°-84.5° C.

NMR(CDCl$_3$)$\delta$: 1.30(6H,t,J=7.3 Hz), 2.73(4H,q,J=7.3 Hz), 6.50(1H,s)

(2) 7-Chloro-4-(4,6-diethyl-2-pyrimidinylthio)quinoline

After dissolving 0.84 g of 4,7-dichloroquinoline and 0.70 g of 4,6-diethyl-2-mercaptopyrimidine in 10 ml of dry dimethylimidazolidinone, the solution was stirred for 2 hours at the room temperature. After finishing the reaction, the reaction mixture was poured into 100 ml of water and extracted 3 times with 75 ml of ethyl acetate. The organic solvent layer was dried over anhydrous sodium sulfate and distilled off the solvent under reduced pressure. The residue was purified by silica gel column chromatography (eluate: n-hexane/ethyl acetate=8/2) to obtain 0.98 g (72% yield) of the desired product 7-chloro-4-(4,6-diethyl-2-pyrimidinylthio)-quinoline. Melting point was 64.8°-66.0° C.

NMR(CDCl$_3$)$\delta$: 1.08(6H,t,J=7.3 Hz), 2.57(4H,q,J=7.3 Hz), 6.73(1H,s), 7.77(1H,dd,J=2.2, 8.8 Hz), 7.87(1H,d,J=4.4 Hz), 7.98(1H,d,J=8.8 Hz), 8.57(1H,d,J=2.2 Hz), 8.88(1H,d,J=4.4 Hz)

Examples of other compounds prepared by carrying out the same procedures as described above are summarized in Table 3.

TABLE 3

| Comp. No. | X | Yn | Z | R$^1$ | R$^2$ | R$^3$ | m.p. (°C.) | NMR (400MH$_z$) (CDCl$_3$;, $\delta$ from TMS) |
|---|---|---|---|---|---|---|---|---|
| 1 | O | 7-Cl | H | OMe | OMe | H | 119~120 | 3.81(6H, s), 5.87(1H, s), 7.30 (1H, d, J=5.1Hz), 7.50(1H, dd, J=2.20, 8.80Hz), 8.06(1H, d, J=8.80Hz), 8.14(1H, d, J=2.20Hz), 8.91(1H, d, J=5.1Hz) |

TABLE 3-continued

| Comp. No. | X | Yn | Z | R¹ | R² | R³ | m.p. (°C.) | NMR (400MHz) (CDCl₃:; δ from TMS) |
|---|---|---|---|---|---|---|---|---|
| 2 | S | 7-Cl | H | Me | Me | H | 127.4 ~ 129.5 | 2.30(6H, s), 6.75(1H, s), 7.47 (1H, m), 7.84(1H, d, J=4.4Hz), 8.12(1H, s), 8.14(1H, m), 8.90 (1H, d, J=4.4Hz) |
| 3 | O | H | H | OMe | OMe | H | 104 ~ 105 | 3.80(6H, s), 5.86(1H, s), 7.30 (1H, d, J=5.2Hz), 7.55(1H, m), 7.75(1H, m), 8.10(1H, d, J=8.1 Hz), 8.93(1H, d, J=5.2Hz) |
| 4 | O | H | Me | OMe | OMe | H | oil | 2.73(3H, s), 3.75(6H, s), 5.80 (1H, s), 7.12(1H, s), 7.50(1H, m), 7.65(1H, m), 8.03(1H, d, J= 8.3Hz), 8.11(1H, d, J=8.3Hz) |
| 5 | O | 6-Cl | H | OMe | OMe | H | 132.0 ~ 133.2 | 3.83(6H, s), 5.88(1H, s), 7.32 (1H, d, J=5.2Hz), 7.68(1H, dd, J=2.2, 8.8Hz), 8.09(1H, d, J=8.8 Hz), 8.11(1H, d, J=2.2Hz), 8.89 (1H, d, J=5.2Hz) |
| 6 | S | 6-Cl | H | Me | Me | H | 88.0 ~ 94.3 | 2.31(6H, s), 6.76(1H, s), 7.63- 7.87(1H, m), 7.85(1H, d, J=4.4 Hz), 8.10(1H, d, J=8.8Hz), 8.29 (1H, d, J=2.2Hz), 8.89(1H, d, J=4.4Hz) |
| 7 | O | 7-F | H | OMe | OMe | H | 120.2 ~ 123.8 | 3.81(6H, s), 5.87(1H, s), 7.27 (1H, d, J=5.1Hz), 7.33(1H, m), 7.75(1H, dd, J=2.9, 9.6Hz), 8.12 (1H, m), 8.91(1H, d, J=5.1Hz) |
| 8 | S | 7-F | H | Me | Me | H | 149.0 ~ 150.5 | 2.31(6H, s), 6.76(1H, s), 7.32 (1H, m), 7.79(1H, m), 7.84(1H, d, J=5.1Hz), 8.28(1H, m), 8.90 (1H, d, J=5.1Hz) |
| 9 | S | 8-Cl | H | Me | Me | H | 145.2 ~ 150.6 | 2.30(6H, s), 6.76(1H, s), 7.46 (1H, t, J=7.3Hz), 7.85(1H, d, J= 7.3Hz), 7.92(1H, d, J=4.4Hz), 8.23(1H, d, J=7.3Hz), 9.03(1 H, d, J=4.4Hz) |
| 10 | O | 6-F | H | OMe | OMe | H | 126.9 ~ 128.1 | 3.81(6H, s), 5.87(1H, s), 7.32 (1H, d, J=4.4Hz), 7.51(1H, m), 7.69(1H, m), 8.13(1H, m), 8.87 (1H, d, J=4.4Hz) |
| 11 | O | 7-Br | H | OMe | OMe | H | 134.8 ~ 138.1— | 3.81(6H, s), 5.87(1H, s), 7.30 (1H, d, J=5.2Hz), 7.62(1H, dd, J=1.5, 8.8Hz), 7.97(1H, d, J=1.5Hz), 8.8 Hz), 8.32(1H, d, J=1.5Hz), 8.90 (1H, d, J=5.2Hz) |
| 12 | S | 7-Br | H | Me | Me | H | 127.7 ~ 131.1 | 2.30(6H, s), 6.76(1H, s), 7.60 (1H, m), 7.85(1H, d, J=4.4Hz), 8.14(1H, d, J=8.8Hz), 8.32(1H, d, J=1.5Hz), 8.89(1H, d, J=4.4Hz) |
| 13 | O | 7-I | H | OMe | OMe | H | 146.0 ~ 147.2 | 3.81(6H, s), 5.87(1H, s), 7.30 (1H, d, J=4.4Hz), 7.80(2H, m), 8.56(1H, d, J=1.5Hz), 8.88(1H, d, J=5.1Hz) |
| 14 | O | 5,7-di-Cl | H | OMe | OMe | H | 56.0 ~ 64.3 | 3.74(6H, s), 5.81(1H, s), 7.23 (1H, d, J=4.4Hz), 7.56(1H, d, J= 2.2Hz)8.09(1H, d, J=2.2Hz), 8.92(1H, d, J=4.4Hz) |
| 15 | S | 5,7-di-Cl | H | Me | Me | H | 182.0 ~ 183.2 | 2.31(6H, s), 6.77(1H, s), 7.58 (1H, d, J=2.2Hz), 7.74(1H, d, J= 4.4Hz), 8.08(1H, d, J=2.2Hz), 8.79(1H, d, J=4.4Hz) |
| 16 | S | 6,7-di-Cl | H | Me | Me | H | 147.9 ~ 148.5 | 2.31(6H, s), 6.77(1H, s), 7.84 (1H, d, J=5.4Hz), 8.27(1H, s), 8.40(1H, s), 8.90(1H, d, J=5.4 Hz) |
| 17 | O | 7-CF₃ | H | OMe | OMe | H | 94.7 ~ 98.6 | 3.82(6H, s), 5.88(1H, s), 7.41 (1H, d, J=4.5Hz), 7.73(1H, d, J= 8.8Hz), 8.24(1H, d, J=8.8Hz), 8.45(1H, s), 9.00(1H, d, J=4.5Hz) |
| 18 | O | 7-OMe | H | OMe | OMe | H | 76.5 ~ 79.2 | 3.80(6H, s), 3.96(3H, s), 5.84 (1H, s), 7.15(1H, d, J=5.2Hz), 7.17(1H, dd, J=2.2, 9.5Hz), 7.44(1H, d, J=2.9Hz), 7.96(1H, d, J=9.5Hz), 8.81(1H, d, J=5.2Hz) |
| 19 | O | 5-Me | H | OMe | OMe | H | 111 ~ 112 | 2.76(3H, s), 3.78(6H, s), 5.83 (1H, s), 7.15(1H, d, J=4.7Hz), 7.31(1H, d, J=7.7Hz), 7.60(1H, t, J=7.7Hz), 8.01(1H, d, J=7.7 Hz), 8.87(1H, d, J=4.7Hz) |
| 20 | O | 7-Br | Me | OMe | OMe | H | 152.0 ~ | 2.73(3H, s), 3.80(6H, s), 5.86 (1H, s), 7.18(1H, s), 7.55(1H, |

TABLE 3-continued

| Comp. No. | X | Yn | Z | R¹ | R² | R³ | m.p. (°C.) | NMR (400MHz) (CDCl₃; δ from TMS) |
|---|---|---|---|---|---|---|---|---|
|  |  |  |  |  |  |  | 153.5 | dd, J=2.2, 8.8Hz), 7.87(1H, d, J=8.8Hz), 8.24(1H, d, J=2.2Hz) |
| 21 | O | 7-Me | H | OMe | OMe | H | 58.1 ~ 64.7 | 2.57(3H, s), 3.79(6H, s), 5.85 (1H, s), 7.23(1H, d, J=5.2Hz), 7.38(1H, dd, J=1.6, 8.8Hz), 7.92 (1H, s), 7.99(1H, d, J=8.8Hz), 8.86(1H, d, J=5.2Hz) |
| 22 | S | 7-Me | H | Me | Me | H | semi-solid | 2.32(6H, s), 2.57(3H, s), 6.74 (1H, s), 7.38(1H, d, J=8.8Hz), 7.72(1H, d, J=4.4Hz), 7.92(1H, s), 8.16(1H, d, J=8.8Hz), 8.86 (1H, d, J=4.4Hz) |
| 23 | S | 7-I | H | H | H | H | 121.4 ~ 124.1 | 7.02(1H, t, J=5.1Hz), 7.79(1H, dd, J=1.5, 8.8Hz), 7.82(1H, d, J=4.4Hz), 7.95(1H, d, J=8.8Hz), 8.44(1H, d, J=5.1Hz), 8.59 (1H, d, J=1.5Hz), 8.91(1H, d, J=4.4Hz) |
| 24 | O | 7-I | H | OEt | OEt | H | 107.3 ~ 108.5 | 1.28(6H, t, J=7.3Hz), 4.19(4H, q, J=7.3Hz), 5.81(1H, s), 7.29 (1H, d, J=5.1Hz), 7.77(1H, dd, J=1.5, 8.8Hz), 7.80(1H, d, J=8.8Hz), 8.56(1H, d, J=1.5Hz), 8.87(1H, d, J=5.1Hz) |
| 25 | O | 5,7-di-Me | H | OMe | OMe | H | 125 ~ 126 | 2.50(3H, s), 2.71(3H, s), 3.77 (6H, s), 5.82(1H, s), 7.07(1H, d, J=5.2Hz), 7.15(1H, s), 7.78 (1H, S), 8.80(1H, d, J=5.2Hz) |
| 26 | S | 5-Cl | Me | Me | Me | H | 145.1 ~ 146.0 | 2.36(6H, s), 2.84(3H, s), 6.84 (1H, s), 7.62(1H, s), 7.65(1H, t, J=8.1Hz), 7.85(1H, d, J=8.1 Hz), 8.37(1H, d, J=8.1Hz) |
| 27 | S | 5,7-di-Cl | H | CF₃ | Me | H | 101.7 ~ 103.2 | 2.46(3H, s), 7.16(1H, s), 7.60 (1H, d, J=2.2Hz), 7.80(1H, d, J=4.4Hz), 8.13(1H, d, J=2.2Hz), 8.88(1H, d, J=4.4Hz) |
| 28 | S | 7-I | H | CF₃ | Me | H | oil | 2.44(3H, s), 7.18(1H, s), 7.80 (1H, dd, J=2.2, 8.8Hz), 7.84(1 H, d, J=4.4Hz), 7.95(1H, d, J=8.8 Hz), 8.60(1H, d, J=2.2Hhz), 8.93(1H, d, J=4.4Hz) |
| 29 | O | 5,7-di-I | H | OMe | OMe | H | 151.5 ~ 153.0 | 3.79(6H, s), 5.87(1H, s), 7.30 (1H, d, J=5.1Hz), 8.54(1H, d, J=1.5Hz), 8.62(1H, d, J=1.5Hz), 8.92(1H, d, J=5.1Hz) |
| 30 | S | 7-Cl | H | OMe | OMe | H | 9.30 ~ 94.5 | 3.55(6H, s), 5.72(1H, s), 7.51 (1H, dd, J=2.2, 9.5Hz), 7.80(1 H, d, J=4.4Hz), 8.14(1H, d, J=2.2 Hz), 8.24(1H, d, J=9.5Hz), 8.92 (1H, d, J=4.4Hz) |
| 31 | S | 5,7-di-Cl | H | OMe | OMe | H | 158.0 ~ 159.2 | 3.53(6H, s), 5.71(1H, s), 7.61 (1H, d, J=2.2Hz), 7.80(1H, d, J=4.4Hz), 8.10(1H, d, J=2.2Hz), 8.85(1H, d, J=4.4Hz) |
| 32 | S | 7-I | H | OMe | OMe | H | 78.0 ~ 80.0 | 3.55(6H, s), 5.71(1H, s), 7.80-7.82(2H, m), 8.00(1H, d, J=8.8 Hz), 8.57(1H, d, J=2.2Hz), 8.90 (1H, d, J=4.4Hz) |
| 33 | S | 7-Cl | H | Me | Et | H | 81.2 ~ 82.7 | 1.03(3H, t, J=7.3Hz), 2.35(3H, s), 2.53(2H, q, J=7.3Hz), 6.74 (1H, s), 7.48(1H, dd, J=1.5, 8.8 Hz), 7.85(1H, d, J=4.4Hz), 8.14 (1H, d, J=1.5Hz), 8.20(1H, d, J=8.8Hz), 8.91(1H, d, J=4.4 Hz) |
| 34 | S | 7-Cl | H | Me | n-Pr | H |  |  |
| 35 | S | 7-Cl | H | Me | i-Pr | H | 110.0 ~ 112.8 | 0.98(6H, d, J=7.3Hz), 2.38(3H, s), 2.64-2.73(1H, m), 6.73(1 H, s), 7.47(1H, dd, J=2.2, 8.8H z), 7.85(1H, d, J=4.4Hz), 8.14 (1H, d, J=2.2Hz), 8.19(1H, d, J=8.8Hz), 8.91(1H, d, J=4.4Hz) |
| 36 | S | 7-Cl | H | Me | n-Bu | H |  |  |
| 37 | S | 7-Cl | H | Me | i-Bu | H | oil | 0.75(6H, d, J=6.6Hz), 1.72-1.79(1H, m), 2.34(2H, d, J=6.6Hz), 2.36(3H, s), 6.69(1H, s), 7.47 (1H, dd, J=2.2, 8.8Hz), 7.83 (1H, d, J=4.4Hz), 8.14(1H, d, J=2.2Hz), 8.20(1H, d, J=8.8Hz), 8.91(1H, d, J=4.4Hz) |

TABLE 3-continued

| Comp. No. | X | Yn | Z | R¹ | R² | R³ | m.p. (°C.) | NMR (400MHz) (CDCl₃;; δ from TMS) |
|---|---|---|---|---|---|---|---|---|
| 38 | S | 7-Cl | H | Me | sec-Bu | H | | |
| 39 | S | 7-Cl | H | Me | t-Bu | H | | |
| 40 | S | 5,7-di-Cl | H | Me | Et | H | 92.9 ~ 94.1 | 1.02(3H, t, J=7.3Hz), 2.35(3H, s), 2.52(2H, q, J=7.3Hz), 6.75 (1H, s), 7.57(1H, d, J=2.2Hz), 7.77(1H, d, J=4.4Hz), 8.09(1 H, d, J=2.2Hz), 8.80(1H, d, J=4.4 Hz) |
| 41 | S | 5,7-di-Cl | H | Me | n-Pr | H | | |
| 42 | S | 5,7-di-Cl | H | Me | i-Pr | H | 74.7 ~ 76.2 | 0.97(6H, d, J=6.6Hz), 2.39(3H, s), 2.63-2.74(1H, m), 6.74(1 H, s), 7.56(1H, d, J=2.2Hz), 7.78 (1H, d, J=4.4Hz), 8.09(1H, d, J=2.2Hz), 8.81(1H, d, J=4.4Hz) |
| 43 | S | 5,7-di-Cl | H | Me | n-Bu | H | | |
| 4 | S | 5,7-di-Cl | H | Me | i-Bu | H | oil | 0.76(6H, d, J=6.6Hz), 1.68-1.72(1H, m), 2.32(2H, d, J=7.3Hz), 2.36(3H, s), 6.69(1H, s), 7.56 (1H, d, J=2.2Hz), 7.75(1H, d, J=4.4Hz), 8.09(1H, d, J=2.2Hz), 8.80(1H, d, J=4.4Hz) |
| 45 | S | 5,7-di-Cl | H | Me | sec-Bu | H | | |
| 46 | S | 5,7-di-Cl | H | Me | t-Bu | H | | |
| 47 | S | 7-Br | H | Me | Et | H | | |
| 48 | S | 7-Br | H | Me | n-Pr | H | | |
| 49 | S | 7-Br | H | Me | i-Pr | H | | |
| 50 | S | 7-Br | H | Me | n-Bu | H | | |
| 51 | S | 7-Br | H | Me | i-Bu | H | | |
| 52 | S | 7-Br | H | Me | sec-Bu | H | | |
| 53 | S | 7-Br | H | Me | t-Bu | H | | |
| 54 | S | 5,7-di-Br | H | Me | Me | H | | |
| 55 | S | 5,7-di-Br | H | Me | Et | H | | |
| 56 | S | 5,7-di-Br | H | Me | n-Pr | H | | |
| 57 | S | 5,7-di-Br | H | Me | i-Pr | H | | |
| 58 | S | 5,7-di-Br | H | Me | n-Bu | H | | |
| 59 | S | 5,7-di-Br | H | Me | i-Bu | H | | |
| 60 | S | 5,7-di-Br | H | Me | sec-Bu | H | | |
| 61 | S | 5,7-di-Br | H | Me | t-Bu | H | | |
| 62 | S | 7-I | H | Me | Me | H | 136.2 ~ 137.1 | 2.30(6H, s), 6.75(1H, s), 7.79 (1H, d, J=8.8Hz), 7.85(1H, d, J=4.4Hz), 7.96(1H, d, J=8.8Hz), 8.57(1H, s), 8.87(1H, d, J=4.4Hz) |
| 63 | S | 7-I | H | Me | Et | H | 70.5 ~ 73.2 | 1.03(3H, t, J=7.3Hz), 2.33(3H, s), 2.52(2H, q, J=7.3Hz), 6.73 (1H, s), 7.75(1H, dd, J=2.2Hz, 8.8Hz), 7.86(1H, d, J=4.4Hz), 7.95(1H, d, J=8.8Hz), 8.55(1 H, d, J=2.2Hz), 8.87(1H, d, J=4.4Hz) |
| 64 | S | 7-I | H | Me | n-Pr | H | | |
| 65 | S | 7-I | H | Me | i-Pr | H | 67.2 ~ 69.3 | 0.98(6H, d, J=7.32Hz), 2.37(3H, s), 2.64-2.73(1H, m), 6.73(1 H, s), 7.57(1H, d, J=8.8, 1.5H z), 7.86(1H, d, J=4.4Hz), 7.95, 1H, d, J=8.8Hz), 8.56(1H, d, J=1.5Hz), 8.88(1H, d, J=4.4Hz) |
| 66 | S | 7-I | H | Me | n-Bu | H | | |
| 67 | S | 7-I | H | Me | i-Bu | H | oil | 0.74(6H, d, J=6.6Hz), 1.72-1.76(1H, m), 2.33(2H, d, J=7.3Hz), 2.36(3H, s), 6.68(1H, s), 7.77 (1H, dd, J=1.5, 8.8Hz), 7.84 (1H, d, J=4.4Hz), 7.96(1H, d, J=8.8Hz), 8.57(1H, d, J=1.5Hz), 8.88(1H, d, J=4.4Hz) |
| 68 | S | 7-I | H | Me | sec-Bu | H | | |
| 69 | S | 7-I | H | Me | t-Bu | H | | |
| 70 | S | 5,7-di-I | H | Me | Me | H | 164.0 ~ 165.5 | 2.28(6H, s), 6.74(1H, s), 7.83 (1H, d, J=5.1Hz), 8.59(2H, s), 8.80(1H, d, J=5.1Hz) |

TABLE 3-continued

| Comp. No. | X | Yn | Z | R¹ | R² | R³ | m.p. (°C.) | NMR (400MHz) (CDCl₃:; δ from TMS) |
|---|---|---|---|---|---|---|---|---|
| 71 | S | 5,7-di-I | H | Me | Et | H | | |
| 72 | S | 5,7-di-I | H | Me | n-Pr | H | | |
| 73 | S | 5,7-di-I | H | Me | i-Pr | H | | |
| 74 | S | 5,7-di-I | H | Me | n-Bu | H | | |
| 75 | S | 5,7-di-I | H | Me | i-Bu | H | | |
| 76 | S | 5,7-di-I | H | Me | sec-Bu | H | | |
| 77 | S | 5,7-di-I | H | Me | t-Bu | H | | |
| 78 | S | 7-Cl | H | Et | Et | H | 64.8 ~ 66.0 | 1.08(6H, t, J=7.3Hz), 2.57(4H, q, J=7.3Hz), 6.73(1H, s), 7.77 (1H, dd, J=2.2, 8.8Hz), 7.87 (1H, d, J=4.4Hz), 7.98(1H, d, J=8.8Hz), 8.57(1H, d, J=2.2Hz), 8.88(1H, d, J=4.4Hz) |
| 79 | S | 7-Cl | H | Et | n-Pr | H | oil | 0.80(3H, t, J=7.3Hz), 1.08(3H, t, J=7.3Hz), 1.42–1.56(2H, m), 2.50(2H, t, J=7.3Hz), 2.56 (2H, q, J=7.3Hz), 6.76(1H, s), 7.48(1H, dd, J=2.2, 8.8Hz), 7.84 (1H, d, J=5.1Hz), 8.15(1H, d, J=2.2Hz), 8.19(1H, d, 8.8Hz), 8.91(1H, d, J=5.1Hz) |
| 80 | S | 7-Cl | H | Et | i-Pr | H | | |
| 81 | S | 7-Cl | H | Et | n-Bu | H | | |
| 82 | S | 7-Cl | H | Et | i-Bu | H | | |
| 83 | S | 7-Cl | H | Et | sec-Bu | H | | |
| 84 | S | 7-Cl | H | Et | t-Bu | H | | |
| 85 | S | 5,7-di-Cl | H | Et | Et | H | 111.7 ~ 113.5 | 1.08(6H, t, J=7.3Hz), 2.58(4H, q, J=7.3Hz), 6.73(1H, s), 7.57 (1H, d, J=2.2Hz), 7.78(1H, d, J=4.4Hz), 8.10(1H, d, J=2.2Hz), 8.80(1H, d, J=4.4Hz) |
| 86 | S | 5,7-di-Cl | H | Et | n-Pr | H | | |
| 87 | S | 5,7-di-Cl | H | Et | i-Pr | H | | |
| 88 | S | 5,7-di-Cl | H | Et | n-Bu | H | | |
| 89 | S | 5,7-di-Cl | H | Et | i-Bu | H | | |
| 90 | S | 5,7-di-Cl | H | Et | sec-Bu | H | | |
| 91 | S | 5,7-di-Cl | H | Et | t-Bu | H | | |
| 92 | S | 7-Br | H | Et | Et | H | | |
| 93 | S | 7-Br | H | Et | n-Pr | H | | |
| 94 | S | 7-Br | H | Et | i-Pr | H | | |
| 94 | S | 7-Br | H | Et | n-Bu | H | | |
| 96 | S | 7-Br | H | Et | i-Bu | H | | |
| 97 | S | 7-Br | H | Et | sec-Bu | H | | |
| 98 | S | 7-Br | H | Et | t-Bu | H | | |
| 99 | S | 5,7-di Br | H | Et | Et | H | | |
| 100 | S | 5,7-di Br | H | Et | n-Pr | H | | |
| 101 | S | 5,7-di Br | H | Et | i-Pr | H | | |
| 102 | S | 5,7-di Br | H | Et | n-Bu | H | | |
| 103 | S | 5,7-di Br | H | Et | i-Bu | H | | |
| 104 | S | 5,7-di Br | H | Et | sec-Bu | H | | |
| 105 | S | 5,7-di Br | H | Et | t-Bu | H | | |
| 106 | S | 7-I | H | Et | Et | H | 59.7 ~ 61.2 | 1.08(6H, t, J=7.3Hz), 2.57(4H, q, J=7.3Hz), 6.73(1H, s), 7.48 (1H, dd, J=2.2, 8.8Hz), 7.85 (1H, d, J=4.4Hz), 8.14(1H, d, J=2.2Hz), 8.21(1H, d, J=8.8Hz), 8.91(1H, d, J=4.4Hz) |
| 107 | S | 7-I | H | Et | n-Pr | H | | |
| 108 | S | 7-I | H | Et | i-Pr | H | | |
| 109 | S | 7-I | H | Et | n-Bu | H | | |
| 110 | S | 7-I | H | Et | i-Bu | H | | |
| 111 | S | 7-I | H | Et | sec-Bu | H | | |
| 112 | S | 7-I | H | Et | t-Bu | H | | |
| 113 | S | 5,7-di-I | H | Et | Et | H | | |
| 114 | S | 5,7-di-I | H | Et | n-Pr | H | | |
| 115 | S | 5,7-di-I | H | Et | i-Pr | H | | |
| 116 | S | 5,7-di-I | H | Et | n-Bu | H | | |

TABLE 3-continued

| Comp. No. | X | Yn | Z | R¹ | R² | R³ | m.p. (°C.) | NMR (400MHz) (CDCl₃; δ from TMS) |
|---|---|---|---|---|---|---|---|---|
| 117 | S | 5,7-di-I | H | Et | i-Bu | H | | |
| 118 | S | 5,7-di-I | H | Et | sec-Bu | H | | |
| 119 | S | 5,7-di-I | H | Et | t-Bu | H | | |
| 120 | S | 7-Cl | H | n-Pr | n-Pr | H | | 0.82(6H, t, J=7.3Hz), 1.98–1.56(4H, m), 2.51(4H, t, J=7.3Hz), 6.70(1H, s), 7.46(1H, dd, J=8.8, 2.2Hz), 7.83(1H, d, J=4.4 Hz), 8.14(1H, d, J=2.2Hz), 8.19 (1H, d, J=8.8Hz), 8.90(1H, d, J=4.4Hz) |
| 121 | S | 7-Cl | H | n-Pr | i-Pr | H | | |
| 122 | S | 7-Cl | H | n-Pr | n-Bu | H | | |
| 123 | S | 7-Cl | H | n-Pr | i-Bu | H | | |
| 124 | S | 7-Cl | H | n-Pr | sec-Bu | H | | |
| 125 | S | 7-Cl | H | n-Pr | t-Bu | H | | |
| 126 | S | 5,7-di-Cl | H | n-Pr | n-Pr | H | | 0.83(6H, t, J=7.3Hz), 1.48–1.56(4H, m), 2.51(4H, t, J=7.3Hz), 6.70(1H, s), 7.55(1H, d, J=2.2 Hz), 7.76(1H, d, J=4.4Hz), 8.09 (1H, d, J=2.2Hz), 8.80(1H, d, J=4.4Hz) |
| 127 | S | 5,7-di-Cl | H | n-Pr | i-Pr | H | | |
| 128 | S | 5,7-di-Cl | H | n-Pr | n-Bu | H | | |
| 129 | S | 5,7-di-Cl | H | n-Pr | i-Bu | H | | |
| 130 | S | 5,7-di-Cl | H | n-Pr | sec-Bu | H | | |
| 131 | S | 5,7-di-Cl | H | n-Pr | t-Bu | H | | |
| 132 | S | 7-Br | H | n-Pr | n-Pr | H | | |
| 133 | S | 7-Br | H | n-Pr | i-Pr | H | | |
| 134 | S | 7-Br | H | n-Pr | n-Bu | H | | |
| 135 | S | 7-Br | H | n-Pr | i-Bu | H | | |
| 136 | S | 7-Br | H | n-Pr | sec-Bu | H | | |
| 137 | S | 7-Br | H | n-Pr | t-Bu | H | | |
| 138 | S | 5,7-di-Br | H | n-Pr | n-Pr | H | | |
| 139 | S | 5,7-di-Br | H | n-Pr | i-Pr | H | | |
| 140 | S | 5,7-di-Br | H | n-Pr | n-Bu | H | | |
| 141 | S | 5,7-di-Br | H | n-Pr | i-Bu | H | | |
| 142 | S | 5,7-di-Br | H | n-Pr | sec-Bu | H | | |
| 143 | S | 5,7-di-Br | H | n-Pr | t-Bu | H | | |
| 144 | S | 7-I | H | n-Pr | n-Pr | H | oil | 0.83(6H, t, J=7.3Hz), 1.47–1.56(4H, m), 2.50(4H, t, J=7.3Hz), 7.27(1H, s), 7.76 (1H, dd, J=8.8, 1.5Hz), 7.85(1H, d, J=4.4Hz), 7.96 (1H, d, J=8.8Hz), 8.56 (1H, d, J=1.5Hz), 8.88(1H, d, J=4.4Hz) |
| 145 | S | 7-I | H | n-Pr | i-Pr | H | | |
| 146 | S | 7-I | H | n-Pr | n-Bu | H | | |
| 147 | S | 7-I | H | n-Pr | i-Bu | H | | |
| 148 | S | 7-I | H | n-Pr | sec-Bu | H | | |
| 149 | S | 7-I | H | n-Pr | t-Bu | H | | |
| 150 | S | 5,7-di-I | H | n-Pr | n-Pr | H | | |
| 151 | S | 5,7-di-I | H | n-Pr | i-Pr | H | | |
| 152 | S | 5,7-di-I | H | n-Pr | n-Bu | H | | |
| 153 | S | 5,7-di-I | H | n-Pr | i-Bu | H | | |
| 154 | S | 5,7-di-I | H | n-Pr | sec-Bu | H | | |
| 155 | S | 5,7-di-I | H | n-Pr | t-Bu | H | | |
| 156 | S | 7-Cl | H | i-Pr | i-Pr | H | | |
| 157 | S | 7-Cl | H | i-Pr | n-Bu | H | | |
| 158 | S | 7-Cl | H | i-Pr | i-Bu | H | | |
| 159 | S | 7-Cl | H | i-Pr | sec-Bu | H | | |
| 160 | S | 7-Cl | H | i-Pr | t-Bu | H | | |
| 161 | S | 5,7-di-Cl | H | i-Pr | i-Pr | H | | |
| 162 | S | 5,7-di-Cl | H | i-Pr | n-Bu | H | | |
| 163 | S | 5,7-di-Cl | H | i-Pr | i-Bu | H | | |
| 164 | S | 5,7-di-Cl | H | i-Pr | sec-Bu | H | | |
| 165 | S | 5,7-di-Cl | H | i-Pr | t-Bu | H | | |
| 166 | S | 7-Br | H | i-Pr | i-Pr | H | | |
| 167 | S | 7-Br | H | i-Pr | n-Bu | H | | |
| 168 | S | 7-Br | H | i-Pr | i-Bu | H | | |
| 169 | S | 7-Br | H | i-Pr | sec-Bu | H | | |
| 170 | S | 7-Br | H | i-Pr | t-Bu | H | | |
| 171 | S | 5,7-di-Br | H | i-Pr | i-Pr | H | | |
| 172 | S | 5,7-di-Br | H | i-Pr | n-Bu | H | | |
| 173 | S | 5,7-di-Br | H | i-Pr | i-Bu | H | | |
| 174 | S | 5,7-di-Br | H | i-Pr | sec-Bu | H | | |
| 175 | S | 5,7-di-Br | H | i-Pr | t-Bu | H | | |
| 176 | S | 7-I | H | i-Pr | i-Pr | H | | |
| 177 | S | 7-I | H | i-Pr | n-Bu | H | | |
| 178 | S | 7-I | H | i-Pr | i-Bu | H | | |

TABLE 3-continued

| Comp. No. | X | Yn | Z | R¹ | R² | R³ | m.p. (°C.) | NMR (400MHz) (CDCl₃;; δ from TMS) |
|---|---|---|---|---|---|---|---|---|
| 179 | S | 7-I | H | i-Pr | sec-Bu | H | | |
| 180 | S | 7-I | H | i-Pr | t-Bu | H | | |
| 181 | S | 5,7-di-I | H | i-Pr | i-Pr | H | | |
| 182 | S | 5,7-di-I | H | i-Pr | n-Bu | H | | |
| 183 | S | 5,7-di-I | H | i-Pr | i-Bu | H | | |
| 184 | S | 5,7-di-I | H | i-Pr | sec-Bu | H | | |
| 155 | S | 5,7-di-I | H | i-Pr | t-Bu | H | | |
| 186 | S | 7-Cl | H | n-Bu | n-Bu | H | | |
| 187 | S | 7-Cl | H | n-Bu | i-Bu | H | | |
| 188 | S | 7-Cl | H | n-Bu | sec-Bu | H | | |
| 189 | S | 7-Cl | H | n-Bu | t-Bu | H | | |
| 190 | S | 5,7-di-Cl | H | n-Bu | n-Bu | H | | |
| 191 | S | 5,7-di-Cl | H | n-Bu | i-Bu | H | | |
| 192 | S | 5,7-di-Cl | H | n-Bu | sec-Bu | H | | |
| 193 | S | 5,7-di-Cl | H | n-Bu | t-Bu | H | | |
| 194 | S | 7-Br | H | n-Bu | n-Bu | H | | |
| 195 | S | 7-Br | H | n-Bu | i-Bu | H | | |
| 196 | S | 7-Br | H | n-Bu | sec-Bu | H | | |
| 197 | S | 7-Br | H | n-Bu | t-Bu | H | | |
| 198 | S | 5,7-di-Br | H | n-Bu | n-Bu | H | | |
| 199 | S | 5,7-di-Br | H | n-Bu | i-Bu | H | | |
| 200 | S | 5,7-di-Br | H | n-Bu | sec-Bu | H | | |
| 201 | S | 5,7-di-Br | H | n-Bu | t-Bu | H | | |
| 202 | S | 7-I | H | n-Bu | n-Bu | H | | |
| 203 | S | 7-I | H | n-Bu | i-Bu | H | | |
| 204 | S | 7-I | H | n-Bu | sec-Bu | H | | |
| 205 | S | 7-I | H | n-Bu | t-Bu | H | | |
| 206 | S | 5,7-di-I | H | n-Bu | n-Bu | H | | |
| 207 | S | 5,7-di-I | H | n-Bu | i-Bu | H | | |
| 208 | S | 5,7-di-I | H | n-Bu | sec-Bu | H | | |
| 209 | S | 5,7-di-I | H | n-Bu | t-Bu | H | | |
| 210 | S | 7-Cl | H | i-Bu | i-Bu | H | | |
| 211 | S | 7-Cl | H | i-Bu | sec-Bu | H | | |
| 212 | S | 7-Cl | H | i-Bu | t-Bu | H | | |
| 213 | S | 5,7-di-Cl | H | i-Bu | i-Bu | H | | |
| 214 | S | 5,7-di-Cl | H | i-Bu | sec-Bu | H | | |
| 215 | S | 5,7-di-Cl | H | i-Bu | t-Bu | H | | |
| 216 | S | 7-Br | H | i-Bu | i-Bu | H | | |
| 217 | S | 7-Br | H | i-Bu | sec-Bu | H | | |
| 218 | S | 7-Br | H | i-Bu | t-Bu | H | | |
| 219 | S | 5,7-di-Br | H | i-Bu | i-Bu | H | | |
| 220 | S | 5,7-di-Br | H | i-Bu | sec-Bu | H | | |
| 221 | S | 5,7-di-Br | H | i-Bu | t-Bu | H | | |
| 222 | S | 7-I | H | i-Bu | i-Bu | H | | |
| 223 | S | 7-I | H | i-Bu | sec-Bu | H | | |
| 224 | S | 7-I | H | i-Bu | t-Bu | H | | |
| 225 | S | 5,7-di-I | H | i-Bu | i-Bu | H | | |
| 226 | S | 5,7-di-I | H | i-Bu | sec-Bu | H | | |
| 227 | S | 5,7-di-I | H | i-Bu | t-Bu | H | | |
| 228 | S | 7-Cl | H | sec-Bu | sec-Bu | H | | |
| 229 | S | 7-Cl | H | sec-Bu | t-Bu | H | | |
| 230 | S | 5,7-di-Cl | H | sec-Bu | sec-Bu | H | | |
| 231 | S | 5,7-di-Cl | H | sec-Bu | t-Bu | H | | |
| 232 | S | 7-Br | H | sec-Bu | sec-Bu | H | | |
| 233 | S | 7-Br | H | sec-Bu | t-Bu | H | | |
| 234 | S | 5,7-di-Br | H | sec-Bu | sec-Bu | H | | |
| 235 | S | 5,7-di-Br | H | sec-Bu | t-Bu | H | | |
| 236 | S | 7-I | H | sec-Bu | sec-Bu | H | | |
| 237 | S | 7-I | H | sec-Bu | t-Bu | H | | |
| 238 | S | 5,7-di-I | H | sec-Bu | sec-Bu | H | | |
| 239 | S | 5,7-di-I | H | sec-Bu | t-Bu | H | | |
| 240 | S | 7-Cl | H | t-Bu | t-Bu | H | | |
| 241 | S | 5,7-di-Cl | H | t-Bu | t-Bu | H | | |
| 242 | S | 7-Br | H | t-Bu | t-Bu | H | | |
| 243 | S | 5,7-di-Br | H | t-Bu | t-Bu | H | | |
| 244 | S | 7-I | H | t-Bu | t-Bu | H | | |
| 245 | S | 5,7-di-Cl | H | t-Bu | t-Bu | H | | |
| 246 | S | 7-Cl | H | Me | Me | Me | 140~141 | 2.19(3H, s), 2.35(6H, s), 7.47(1H, dd, J=2.2, 8.8 Hz), 7.83(1H, d, J=4.4Hz), 8.14(1H, d, J=2.2Hz), 8.20(1H, d, J=8.8Hz), 8.91(1H, d, J=4.4Hz) |
| 247 | S | 5,7-di-Cl | H | Me | Me | Me | 177~178 | 2.19(3H, s), 2.36(6H, s), 7.58(1H, d, J=2.2Hz), 7.65 (1H, d, J=5.1Hz), 8.07(1 H, d, J=2.2Hz), 8.74(1H, d, J=5.1Hz) |
| 248 | S | 7-I | H | Me | Me | Me | 95~96 | 2.19(3H, s), 2.35(6H, s), 7.77(1H, dd, J=1.5, 8.8Hz), |

TABLE 3-continued

| Comp. No. | X | Yn | Z | R¹ | R² | R³ | m.p. (°C.) | NMR (400MHz) (CDCl₃;; δ from TMS) |
|---|---|---|---|---|---|---|---|---|
| 249 | S | 5,7-di-Cl | H | Me | Me | Et | 124.7 ~ 125.7 | 7.87(1H, d, J=4.4Hz), 7.97 (1H, d, J=8.8Hz), 8.57 (1H, d, J=1.5Hz), 8.88(1H, d, J=4.4Hz) 1.13(3H, t, J=7.3Hz), 2.37 (6H, s), 260(2H, q, J=7.3 Hz), 7.57(1H, d, J=2.2Hz), 7.69(1H, d, J=4.4Hz), 8.06 (1H, d, J=2.2Hz), 8.74(1 H, d, J=4.4Hz) |
| 250 | O | 7-Cl | H | Me | OMe | H | | |
| 251 | O | 5,7-di-Cl | H | Me | OMe | H | | |
| 252 | O | 7-Br | H | Me | OMe | H | | |
| 253 | O | 5,7-di-Br | H | Me | OMe | H | | |
| 254 | O | 7-I | H | Me | OMe | H | | |
| 255 | O | 5,7-di-I | H | Me | OMe | H | | |
| 256 | S | 7-Cl | H | Me | OMe | H | | |
| 257 | S | 5,7-di-Cl | H | Me | OMe | H | | |
| 258 | S | 7-Br | H | Me | OMe | H | | |
| 259 | S | 5,7-di-Br | H | Me | OMe | H | | |
| 260 | S | 7-I | H | Me | OMe | H | | |
| 261 | S | 5,7-di-I | H | Me | OMe | H | | |
| 262 | O | 7-Cl | H | Me | Me | H | 104 ~ 105 | 2.46(6H, s), 6.91(1H, s), 7.27(1H, d, J=4.4Hz), 7.50 (1H, dd, J=2.2, 8.8Hz), 8.13 (1H, d, J=8.8Hz), 8.14 (1H, d, J=2.2Hz), 8.89(1H, d, J=4.4Hz) |
| 263 | S | 7-Cl | H | OMe | OMe | H | 93.0 ~ 94.5 | 3.55(6H, s), 5.72(1H, s), 7.51(1H, dd, J=2.2, 9.5Hz), 7.80(1H, d, J=4.4Hz), 8.14 (1H, d, J=2.2Hz), 8.24 (1H, d, J=9.5Hz), 8.92(1H, d, J=4.4Hz) |

FORMULATION EXAMPLE AND PHYSIOLOGICAL TEST EXAMPLE

Formulation examples and physiological test examples on the agri-horticultural fungicide of the present invention will be illustrated hereinafter.

Formulation Example 1 (dust formulation)

A dust formulation containing 2% of the active ingredient was prepared by uniformly mixing and grinding 2 parts of Compound No. 1 and 98 parts of clay.

Formulation Example 2 (wettable powder)

A wettable powder which had a uniform composition, was a very fine powder and contained 20% of the active ingredient was prepared by uniformly mixing and grinding 10 parts of Compound No. 1, 70 parts of kaolin, 18 parts of white carbon and 2 parts of calcium alkylbenzenesulfonate.

Formulation Example 3 (wettable powder)

A wettable powder which had a uniform composition, was a very fine powder and contained 20% of the active ingredient was prepared by uniformly mixing and grinding 20 parts of Compound No. 2, 3 parts of calcium alkylbenzenesulfonate, 5 parts of polyoxyethylene nonylphenyl ether and 72 parts of acid clay.

Formulation Example 4 (wettable powder)

A wettable powder which was a very fine powder and contained 70% of the active ingredient was prepared by uniformly mixing and grinding 70 parts of Compound No. 3, 2 parts of calcium alkylbenzenesulfonate and 28 parts of diatomaceous earth.

Formulation Example 5 (wettable powder)

A wettable powder containing 50% of the active ingredient was prepared by mixing and grinding 50 parts of Compound No. 1, 1 part of sodium ligninsulfonate, 5 parts of white carbon and 44 parts of diatomaceous earth.

Formulation Example 6 (floable formulation)

A floable formulation containing 40% of the active ingredient was prepared by using a sand grinder and wet grinding a mixture composed of 40 parts of Compound No. 3, 3 parts of carboxymethyl cellulose, 2 parts of sodium ligninsulfonate, 1 part of sodium dio ctylsulfosuccinate and 54 parts of water.

Formulation Example 7 (emulsifiable concentrate)

An emulsifiable concentrate containing 10% of the active ingredient was prepared by mixing and dissolving 10 parts of Compound No. 3, 70 parts of xylene and 20 parts of polyoxyethylene nonylphenyl ether.

TEST EXAMPLE 1

Controlling test for cucumber powdery mildew

The wettable powder obtained in Formulation Example 2 was diluted to a prescribed concentration and sprayed in 50 ml portions for 3 pots on the first leaf seedlings of cucumber (cultivar; Forcing Nippon) which had been grown in a green house on pots of 7.5 cm in diameter.

After air-drying the chemical, conidia of Sphaerotheca fuliginea (cucumber powdery mildew) which had previously been developed on cucumber leaves were lightly shaken off on the seedlings to carry out inoculation. After 10 days from the inoculation, lesion area per leaf by cucumber powdery mildew was inspected in accordance with the following index. Results are illustrated in Table 2 (Tables 5-7).

Severity
- 0: No lesion is observed.
- 1: Lesion area is 5% or less.
- 2: Lesion area is from 5 to 25%.
- 3: Lesion area is from 25 to 50%.
- 4: Lesion area is 50% or more.

$$\text{Preventive value (\%)} = \left(1 - \frac{\text{severity in treated area}}{\text{severity in untreated area}}\right) \times 100$$

Chemical injury was judged on the basis of the following standard.

Chemical injury standard
- −: No injury is observed.
- ±: Slight injury is observed in some seedlings.
- +: Slight injury is observed in all seedlings.
- ++: Medium injury is observed, but the injury can be recovered.
- +++: Injury cannot be recovered.

Chemical injury symptom of cucumber:
Peripheral growth of a leaf stops and curvature of the leaf takes place.

Comparative chemicals 1 and 2 indicates the following compounds, respectively (the same as in Test Example 2).

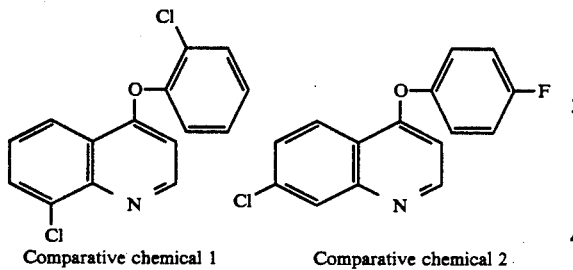

Comparative chemical 1    Comparative chemical 2

Comparative chemicals 1 and 2 are compounds disclosed in Japanese Laid-Open patent HEI 1-246263 (1989).

TABLE 4

| Controlling test for cucumber powdery mildew | | | |
|---|---|---|---|
| Comp. No. | Concentration (ppm) | Preventive Value (%) | Chemical injury |
| 1 | 100 | 100 | — |
|   | 25  | 100 | — |
| 2 | 100 | 100 | — |
|   | 25  | 100 | — |
| 3 | 100 | 100 | — |
|   | 25  | 100 | — |
| 4 | 100 | 100 | — |
|   | 25  | 100 | — |
| 5 | 100 | 100 | — |
|   | 25  | 100 | — |
| 6 | 100 | 100 | — |
|   | 25  | 100 | — |
| 7 | 100 | 100 | — |
|   | 25  | 100 | — |
| 8 | 100 | 100 | — |
|   | 25  | 100 | — |
| 9 | 100 | 100 | — |
|   | 25  | 100 | — |
| 10 | 100 | 100 | — |
|    | 25  | 100 | — |
| 11 | 100 | 100 | — |
|    | 25  | 100 | — |
| 12 | 100 | 100 | — |

TABLE 4-continued

| Controlling test for cucumber powdery mildew | | | |
|---|---|---|---|
| Comp. No. | Concentration (ppm) | Preventive Value (%) | Chemical injury |
|    | 25  | 100 | — |
| 13 | 100 | 100 | — |
|    | 25  | 100 | — |
| 14 | 100 | 100 | — |
|    | 25  | 100 | — |
| 15 | 100 | 100 | — |
|    | 25  | 100 | — |
| 16 | 100 | 100 | — |
|    | 25  | 100 | — |
| 17 | 100 | 100 | — |
|    | 25  | 100 | — |
| 18 | 100 | 100 | — |
|    | 25  | 100 | — |
| 19 | 100 | 100 | — |
|    | 25  | 100 | — |
| 20 | 100 | 100 | — |
|    | 25  | 100 | — |
| 21 | 100 | 100 | — |
|    | 25  | 100 | — |
| 22 | 100 | 100 | — |
|    | 25  | 100 | — |
| 23 | 100 | 100 | — |
|    | 25  | 100 | — |
| 24 | 100 | 100 | — |
|    | 25  | 100 | — |
| 25 | 100 | 100 | — |
|    | 25  | 100 | — |
| 26 | 100 | 100 | — |
|    | 25  | 100 | — |
| 27 | 100 | 100 | — |
|    | 25  | 100 | — |
| 28 | 100 | 100 | — |
|    | 25  | 100 | — |
| 29 | 100 | 100 | — |
|    | 25  | 100 | — |
| 30 | 100 | 100 | — |
|    | 25  | 100 | — |
| 31 | 100 | 100 | — |
|    | 25  | 100 | — |
| 32 | 100 | 100 | — |
|    | 25  | 100 | — |
| 33 | 100 | 100 | — |
|    | 25  | 100 | — |
| 37 | 100 | 100 | — |
|    | 25  | 100 | — |
| 40 | 100 | 100 | — |
|    | 25  | 100 | — |
| 44 | 100 | 100 | — |
|    | 25  | 100 | — |
| 62 | 100 | 100 | — |
|    | 25  | 100 | — |
| 63 | 100 | 100 | — |
|    | 25  | 100 | — |
| 67 | 100 | 100 | — |
|    | 25  | 100 | — |
| 78 | 100 | 100 | — |
|    | 25  | 100 | — |
| 85 | 100 | 100 | — |
|    | 25  | 100 | — |
| 106 | 100 | 100 | — |
|     | 25  | 100 | — |
| 246 | 100 | 100 | — |
|     | 25  | 100 | — |
| 247 | 100 | 100 | — |
|     | 25  | 100 | — |
| 248 | 100 | 100 | — |
|     | 25  | 100 | — |
| 249 | 100 | 100 | — |
|     | 25  | 100 | — |
| 263 | 100 | 100 | — |
|     | 25  | 100 | — |
| Comp. Chemical 1 | 100 | 0 | — |
| Comp. Chemical 2 | 100 | 100 | ++ |
|                  | 25  | 100 | + |
| Untreated Area | — | 0 | — |

TEST EXAMPLE 2

Controlling test for barley powdery mildew

The wettable powder obtained in Formulation Example 3 was diluted to a prescribed concentration and sprayed in 50 ml portions for 3 pots on the first leaf seedlings of barley (cultivar; Azuma Golden) which had been grown in a greenhouse on vinyl pots of 7.5 cm in diameter. The next day, conidia of *Erysiphe graminis* (barley powdery mildew) which had previously been developed on barley leaves were lightly shaken off on the seedlings to carry out inoculation. After 10 days from the inoculation, the number of colony per leaf of barley powdery mildew was counted and preventive value (%) was calculated from the following equation. Results are illustrated in Table 5.

$$\text{Preventive value (\%)} = \left(1 - \frac{\text{the number of colony per leaf in sprayed area}}{\text{the number of colony per leaf in untreated area}}\right) \times 100$$

TABLE 5

Controlling test for barley powdery mildew

| Comp. No. | Concentration (ppm) | Preventive Value (%) | Chemical injury |
|---|---|---|---|
| 1 | 100 | 100 | — |
|   | 25 | 100 | — |
| 2 | 100 | 100 | — |
|   | 25 | 100 | — |
| 3 | 100 | 100 | — |
|   | 25 | 100 | — |
| 4 | 100 | 100 | — |
|   | 25 | 100 | — |
| 5 | 100 | 100 | — |
|   | 25 | 100 | — |
| 6 | 100 | 100 | — |
|   | 25 | 100 | — |
| 7 | 100 | 100 | — |
|   | 25 | 100 | — |
| 8 | 100 | 100 | — |
|   | 25 | 100 | — |
| 9 | 100 | 100 | — |
|   | 25 | 100 | — |
| 10 | 100 | 100 | — |
|   | 25 | 100 | — |
| 11 | 100 | 100 | — |
|   | 25 | 100 | — |
| 12 | 100 | 100 | — |
|   | 25 | 100 | — |
| 13 | 100 | 100 | — |
|   | 25 | 100 | — |
| 14 | 100 | 100 | — |
|   | 25 | 100 | — |
| 15 | 100 | 100 | — |
|   | 25 | 100 | — |
| 16 | 100 | 100 | — |
|   | 25 | 100 | — |
| 17 | 100 | 100 | — |
|   | 25 | 100 | — |
| 18 | 100 | 100 | — |
|   | 25 | 100 | — |
| 19 | 100 | 100 | — |
|   | 25 | 100 | — |
| 20 | 100 | 100 | — |
|   | 25 | 100 | — |
| 21 | 100 | 100 | — |
|   | 25 | 100 | — |
| 22 | 100 | 100 | — |
|   | 25 | 100 | — |
| 23 | 100 | 100 | — |
|   | 25 | 100 | — |
| 24 | 100 | 100 | — |
|   | 25 | 100 | — |
| 25 | 100 | 100 | — |
|   | 25 | 100 | — |
| 26 | 100 | 100 | — |
|   | 25 | 100 | — |
| 27 | 100 | 100 | — |
|   | 25 | 100 | — |
| 28 | 100 | 100 | — |
|   | 25 | 100 | — |
| 29 | 100 | 100 | — |
|   | 25 | 100 | — |
| 30 | 100 | 100 | — |
|   | 25 | 100 | — |
| 31 | 100 | 100 | — |
|   | 25 | 100 | — |
| 32 | 100 | 100 | — |
|   | 25 | 100 | — |
| 33 | 100 | 100 | — |
|   | 25 | 100 | — |
| 37 | 100 | 100 | — |
|   | 25 | 100 | — |
| 40 | 100 | 100 | — |
|   | 25 | 100 | — |
| 44 | 100 | 100 | — |
|   | 25 | 100 | — |
| 62 | 100 | 100 | — |
|   | 25 | 100 | — |
| 63 | 100 | 100 | — |
|   | 25 | 100 | — |
| 67 | 100 | 100 | — |
|   | 25 | 100 | — |
| 78 | 100 | 100 | — |
|   | 25 | 100 | — |
| 85 | 100 | 100 | — |
|   | 25 | 100 | — |
| 106 | 100 | 100 | — |
|   | 25 | 100 | — |
| 246 | 100 | 100 | — |
|   | 25 | 100 | — |
| 247 | 100 | 100 | — |
|   | 25 | 100 | — |
| 248 | 100 | 100 | — |
|   | 25 | 100 | — |
| 249 | 100 | 100 | — |
|   | 25 | 100 | — |
| 263 | 100 | 100 | — |
|   | 25 | 100 | — |
| Comp. Chemical 1 | 100 | 0 | — |
| Untreated Area | — | 0 | |

The results of Test Examples 1 and 2 illustrate that the compound represented by the formula (I) of the present invention exhibits an excellent controlling effect on cucumber powdery mildew and barley powdery mildew and additionally is safe for crop plants. On the other hand, reference tests illustrate that comparative chemical 1 has no effect and comparative chemical 2 has controlling effect but causes chemical injury for cucumber.

What is claimed is:

1. A pyrimidinyloxy(thio)quinoline derivative represented by the formula (I):

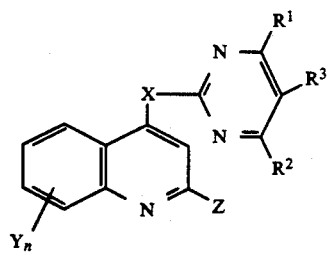
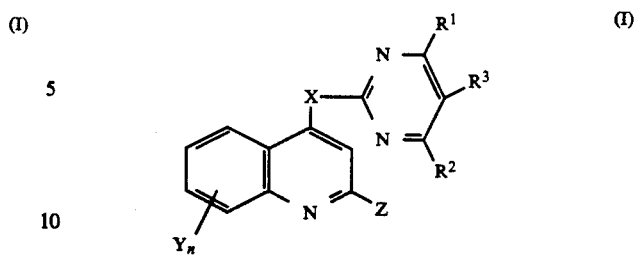

wherein X is an oxygen atom or sulfur atom, Y is a hydrogen atom, halogen atom, alkyl having from 1 to 3 carbon atoms, alkoxy having from 1 to 3 carbon atoms, or trifluoromethyl, Z is a hydrogen atom or methyl, each of $R^1$ and $R^2$ is individually an alkyl having from 1 to 4 carbon atoms, alkoxy having from 1 to 3 carbon atoms, trifluoromethyl or hydrogen atom, $R^3$ is a hydrogen atom or alkyl having from 1 to 2 carbon atoms, and n is an integer of 1 or 2.

2. The compound of claim 1 wherein Z is a hydrogen atom in the formula (I).

3. The compound of claim 1 wherein Z is a hydrogen atom and Y is a halogen atom in the formula (I).

4. The compound of claim 1 wherein Z and $R^3$ are hydrogen atoms and Y is a halogen atom in the formula (I).

5. A pyrimidinyloxy(thio)quinoline derivative of claim 1, wherein X is an oxygen atom or sulfur atom, Y is 7-halo or 5,7-dihalo, Z is a hydrogen atom, $R^1$ and $R^2$ each are alkyl of 1 to 3 carbon atoms or methoxy and $R^3$ is a hydrogen atom.

6. A pyrimidinyloxy(thio)quinoline derivative of claim 1, wherein X is a sulfur atom, Y is 5,7-dichloro, Z is a hydrogen atom, $R^1$ and $R^2$ each are ethyl and $R^3$ is a hydrogen atom.

7. A pyrimidinyloxy(thio)quinoline derivative of claim 1, wherein X is a sulfur atom, Y is 5,7-dichloro, Z is a hydrogen atom, $R^1$ is an ethyl group, $R^2$ is an n-propyl group and $R^3$ is a hydrogen atom.

8. A pyrimidinyloxy(thio)quinoline derivative of claim 1, wherein X is an oxygen atom, Y is 7-iodo, Z is a hydrogen atom, $R^1$ and $R^2$ each are methoxy, $R^3$ is a hydrogen atom.

9. An agri-horticultural fungicide composition comprising, as an active ingredient in admixture with a carrier, a fungically effective amount of a pyrimidinyloxy(thio)quinoline derivative represented by the formula (I):

wherein X is an oxygen atom or sulfur atom, Y is a hydrogen atom, halogen atom, alkyl having from 1 to 3 carbon atoms, alkoxy having from 1 to 3 carbon atoms, or trifluoromethyl, Z is a hydrogen atom or methyl, each of $R^1$ and $R^2$ is individually an alkyl having from 1 to 4 carbon atoms, alkoxy having from 1 to 3 carbon atoms, trifluoromethyl or a hydrogen atom, $R^3$ is a hydrogen atom or alkyl having from 1 to 2 carbon atoms, and n is an integer of 1 or 2.

10. An agri-horticultural fungicide composition according to claim 9, wherein Z is a hydrogen atom in the formula (I).

11. An agri-horticultural fungicide composition according to claim 9, wherein Z is a hydrogen atom and Y is a halogen atom in the formula (I).

12. An agri-horticultural fungicide composition according to claim 9, wherein Z and $R^3$ are hydrogen atoms and Y is a halogen atom in the formula (I).

13. An agri-horticultural fungicide composition according to claim 9, wherein X is a sulfur atom, Y is 5,7-dichloro, Z is a hydrogen atom, $R^1$ and $R^2$ each are ethyl and $R^3$ is a hydrogen atom.

14. An agri-horticultural fungicide composition according to claim 9, wherein X is a sulfur atom, Y is 5,7-dichloro, Z is a hydrogen atom, $R^1$ is an ethyl group, $R^2$ is an n-propyl group and $R^3$ is a hydrogen atom.

15. An agri-horticultural fungicide composition according to claim 9, wherein X is an oxygen atom, Y is 7-iodo, Z is a hydrogen atom, $R^1$ and $R^2$ each are methoxy, $R^3$ is a hydrogen atom.

16. A method for controlling plant disease comprising applying the compound of claim 1 to plant pathogenic fungi or their habitat.

17. A method of claim 16 wherein the compound of claim 1 is applied as an active ingredient in an amount of from 2 to 200 g/ha.

18. An method according to claim 16, wherein Z is a hydrogen atom in the formula (I).

19. An method according to claim 16, wherein Z is a hydrogen atom and Y is a halogen atom in the formula (I).

20. An method according to claim 16, wherein Z and $R^3$ are hydrogen atoms and Y is a halogen atom in the formula (I).

* * * * *